United States Patent
Ogino

(10) Patent No.: US 12,072,964 B2
(45) Date of Patent: Aug. 27, 2024

(54) BIOMETRIC AUTHENTICATION SYSTEM, BIOMETRIC AUTHENTICATION METHOD, AND RECORDING MEDIUM

(71) Applicant: NEC Corporation, Tokyo (JP)

(72) Inventor: Yuka Ogino, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/768,565

(22) PCT Filed: Dec. 6, 2021

(86) PCT No.: PCT/JP2021/044760
§ 371 (c)(1),
(2) Date: Apr. 13, 2022

(87) PCT Pub. No.: WO2022/176323
PCT Pub. Date: Aug. 25, 2022

(65) Prior Publication Data
US 2024/0104179 A1    Mar. 28, 2024

(30) Foreign Application Priority Data

Feb. 18, 2021 (JP) ................................. 2021-024286

(51) Int. Cl.
*G06F 21/32* (2013.01)
*G06V 40/10* (2022.01)
*G06V 40/18* (2022.01)

(52) U.S. Cl.
CPC ............ *G06F 21/32* (2013.01); *G06V 40/103* (2022.01); *G06V 40/18* (2022.01)

(58) Field of Classification Search
None
See application file for complete search history.

(56) References Cited

U.S. PATENT DOCUMENTS 8,649,569 B2 * 2/2014 Shindo .................. G06V 40/67
382/115
9,298,996 B2 * 3/2016 Nada .................. G06V 40/1306
(Continued)

FOREIGN PATENT DOCUMENTS

CN         206769697 U      12/2017
EP         2842489 A1 *     3/2015     ........... A61B 5/1171
(Continued)

OTHER PUBLICATIONS

International Search Report for PCT Application No. PCT/JP2021/044760, mailed on Feb. 8, 2022.
(Continued)

*Primary Examiner* — Joseph P Hirl
*Assistant Examiner* — Hassan Saadoun
(74) *Attorney, Agent, or Firm* — Sughrue Mion, PLLC

(57) ABSTRACT

A biometric authentication system (10) comprises a first imaging unit (11) that images a first image including a living body; a detecting unit (115) that detects a position of the living body in the first image; a second imaging unit (120) that images a second image including an authentication portion of the living body, based on the position of the living body in the first image; a calculating unit (140) that calculates an error between the first imaging unit and the second imaging unit based on the position of the living body in the first image and a position of the authentication portion in the second image; and an adjusting unit (150) that adjusts a set value relating to the second imaging unit, based on the error.

11 Claims, 16 Drawing Sheets

(56) References Cited

U.S. PATENT DOCUMENTS

| | | | |
|---|---|---|---|
| 2011/0274318 A1* | 11/2011 | Shindo | G06V 40/11 382/115 |
| 2012/0200689 A1 | 8/2012 | Friedman et al. | |
| 2018/0173976 A1* | 6/2018 | Hama | G06F 18/22 |
| 2022/0043895 A1* | 2/2022 | Nakazaki | G06F 18/256 |
| 2022/0130173 A1 | 4/2022 | Inoue | |
| 2022/0139112 A1 | 5/2022 | Chono et al. | |
| 2022/0406095 A1* | 12/2022 | Funayama | G06V 40/161 |

FOREIGN PATENT DOCUMENTS

| | | |
|---|---|---|
| JP | 2003-030633 A | 1/2003 |
| JP | 2007-082655 A | 4/2007 |
| JP | 2008-041034 A | 2/2008 |
| JP | 2017-097741 A | 6/2017 |
| JP | 2020-144692 A | 9/2020 |
| WO | 2020/170915 A1 | 8/2020 |
| WO | 2020/183732 A1 | 9/2020 |

OTHER PUBLICATIONS

JP Office Action for JP Application No. 2023-500554, mailed Jul. 2, 2024 with English Translation.

* cited by examiner

BIOMETRIC AUTHENTICATION SYSTEM, BIOMETRIC AUTHENTICATION METHOD, AND RECORDING MEDIUM

This application is a National Stage Entry of PCT/JP2021/044760 filed on Dec. 6, 2021, which claims priority from Japanese Patent Application 2021-024286 filed on Feb. 18, 2021, the contents of all of which are incorporated herein by reference, in their entirety.

TECHNICAL FIELD

This disclosure relates to the art of a biometric authentication system, a biometric authentication method, and a recording medium each for implementing authentication processing relating to a living body.

BACKGROUND ART

As this type system, there is known systems which implement authentication processing (so-called iris authentication) using an iris of a living body. For example, Patent Document 1 discloses an iris authentication apparatus using a wide camera for imaging a whole of a target and a narrow camera for imaging the iris of the target. In Patent Document 2, it is disclosed that the center coordinates of the iris is temporarily stored, and a correction to the center coordinates is added. In Patent Document 3, disclosed is a technique that information and the like of an iris imaging device which has previously imaged an eye-area is stored, and a gaze region is adjusted when the same target is biometrically authenticated again. In Patent Document 4, disclosed is a technique that a line of sight of a verification target person is detected and an iris image is taken by a camera according to a direction of the line of sight detected.

CITATION LIST

Patent Document

Patent Document 1: JP 2003-030633 A
Patent Document 2: JP 2008-041034 A
Patent Document 3: WO 2020/170915 A1
Patent Document 4: WO 2020/183732 A1

SUMMARY

Technical Problem

This disclosure has been made, for example, in view of the above-mentioned cited documents, and an object thereof is to provide a biometric authentication system, biometric authentication method, and recording medium each capable of properly implementing authentication processing relating to a living body.

Solution to Problem

One aspect of a biometric authentication system of this disclosure, comprises: a first imaging unit that images a first image including a living body; a detecting unit that detects a position of the living body in the first image; a second imaging unit that images a second image including an authentication portion of the living body, based on the position of the living body in the first image; a calculating unit that calculates an error between the first imaging unit and the second imaging unit based on the position of the living body in the first image and a position of the authentication portion in the second image; and an adjusting unit that adjusts a set value relating to the second imaging unit, based on the error.

One aspect of a biometric authentication method of this disclosure, comprises: imaging a first image including a living body with a first imaging unit; detecting a position of the living body in the first image; imaging with a second imaging unit, a second image including an authentication portion of the living body, based on the position of the living body in the first image; calculating an error between the first imaging unit and the second imaging unit based on the position of the living body in the first image and a position of the authentication portion in the second image; and adjusting a set value relating to the second imaging unit, based on the error.

One aspect of a recording medium of this disclosure, stores a computer program that causes a computer to perform the following operations: imaging a first image including a living body with a first imaging unit; detecting a position of the living body in the first image; imaging with a second imaging unit, a second image including an authentication portion of the living body, based on the position of the living body in the first image; calculating an error between the first imaging unit and the second imaging unit based on the position of the living body in the first image and a position of the authentication portion in the second image; and adjusting a set value relating to the second imaging unit, based on the error.

DESCRIPTION OF EXAMPLE EMBODIMENTS

Figure 1:
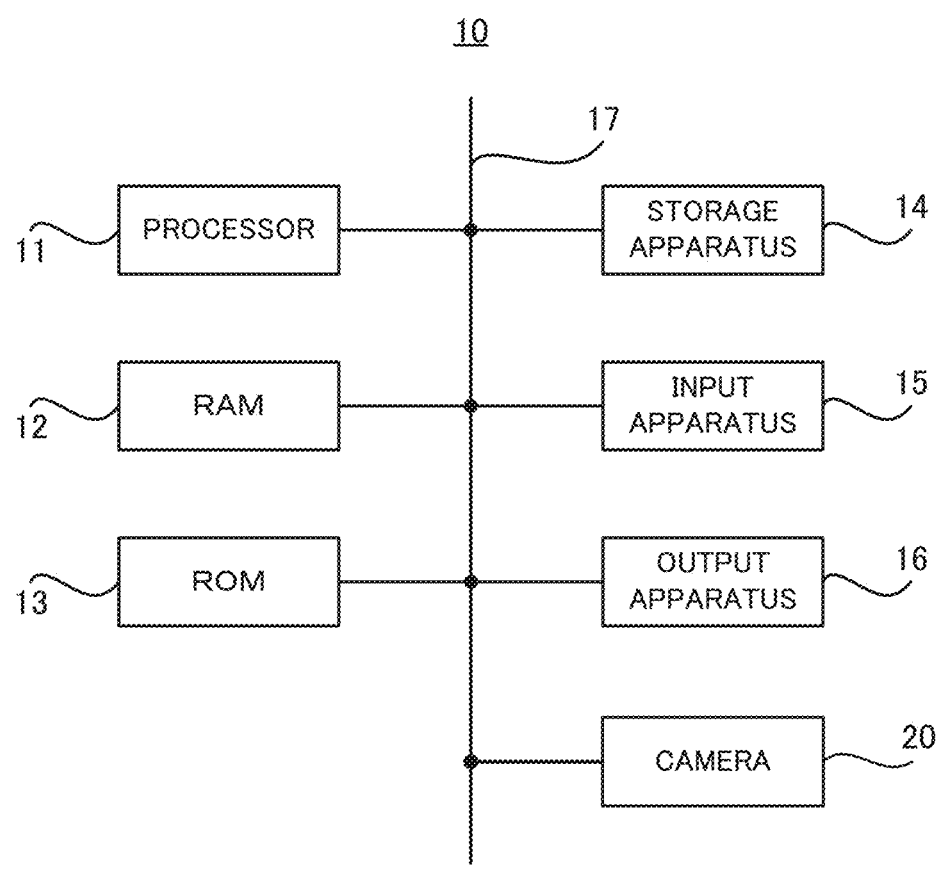
FIG. 1 is a block diagram showing a hardware configuration of a biometric authentication system according to the first example embodiment.

Hereinafter, referring to the drawings, example embodiments of the biometric authentication system, the biometric authentication method, the computer program, and the recording medium will be described below.

First Example Embodiment

A biometric authentication system according to the first example embodiment will be described with reference to FIGS. 1 to 3.
(Hardware Configuration)

First, referring to FIG. 1, a hardware configuration of a biometric authentication system 10 according to a first example embodiment will be described. FIG. 1 is a block diagram showing the hardware configuration of the biometric authentication system 10 according to the first example embodiment.

As shown in FIG. 1, the biometric authentication system 10 according to the first example embodiment comprises a processor 11, a RAM (Random Access Memory) 12, a ROM (Read Only Memory) 13, and a storage apparatus 14. The biometric authentication system 10 may also comprise an input apparatus 15 and an output apparatus 16. The biometric authentication system further comprises a camera 20. The processor 11, the RAM12, the ROM13, the storage apparatus 14, the input apparatus 15, the output apparatus 16, and the camera 20 are connected with each other via a data bus 17.

The Processor 11 reads a computer program. For example, the processor 11 is configured to read a computer program stored in at least one of the RAM12, the ROM13 and the storage apparatus 14. Alternatively, the processor 11 may read a computer program stored in a computer readable recording medium using a recording medium reading apparatus (not illustrated). The processor 11 may acquire (i.e., read) a computer program from an apparatus (not illustrated) located external to the biometric authentication system 10 via a network interface. The processor 11 controls the RAM12, the storage apparatus 14, the input apparatus 15, and the output apparatus 16 by implementing the computer program read. In particular, in the present example embodiment, when the computer program read by the processor 11 is implemented, functional blocks for imaging a target and implementing authentication processing are realized in the processor 11. As the processor 11, one of the CPU (Central Processing Unit), GPU (Graphics Processing Unit), FPGA (field-programmable gate array), DSP (Demand-Side Platform), and ASIC (Application Specific Integrated Circuit) may be used, or two or more of them may be used in parallel.

The RAM12 temporarily stores the computer program which the processor 11 implements. The RAM12 temporarily stores data which the processor 11 temporarily uses when being implementing a computer program. The RAM12 may be, for example, a D-RAM (Dynamic RAM).

The ROM13 stores the computer program to be implemented by the processor 11. The ROM13 may further store fixed data. The ROM13 may be, for example, a P-ROM (Programmable ROM).

The storage apparatus 14 stores data that the biometric authentication system 10 should preserve over a long period of time. The storage apparatus 14 may operate as a temporary storage apparatus of the processor 11. The storage apparatus 14 may include, for example, at least one of a hard disk apparatus, a magnet-optical disk apparatus, an SSD (Solid State Drive), and a disk array apparatus.

The input apparatus 15 is an apparatus that receives input instructions from a user of the biometric authentication system 10. The input apparatus 15 may include, for example, at least one of a keyboard, a mouse, and a touch panel.

The output apparatus 16 is an apparatus that outputs information relating to the biometric authentication system 10 to the outside. For example, the output apparatus 16 may be a display apparatus (e.g., a display) capable of displaying information relating to the biometric authentication system 10.

The camera 20 is configured as an apparatus capable of taking an image. The camera 20 may be a visible light camera or may be an image camera which takes an image by light other than visible light, such as an infrared camera. The camera 20 may be a camera for taking still images or may be a camera for videos. There may be provided more than one of the camera 20. A more specific configuration of the camera 20 will be described in detail later.
(Functional Configuration)

Figure 2:
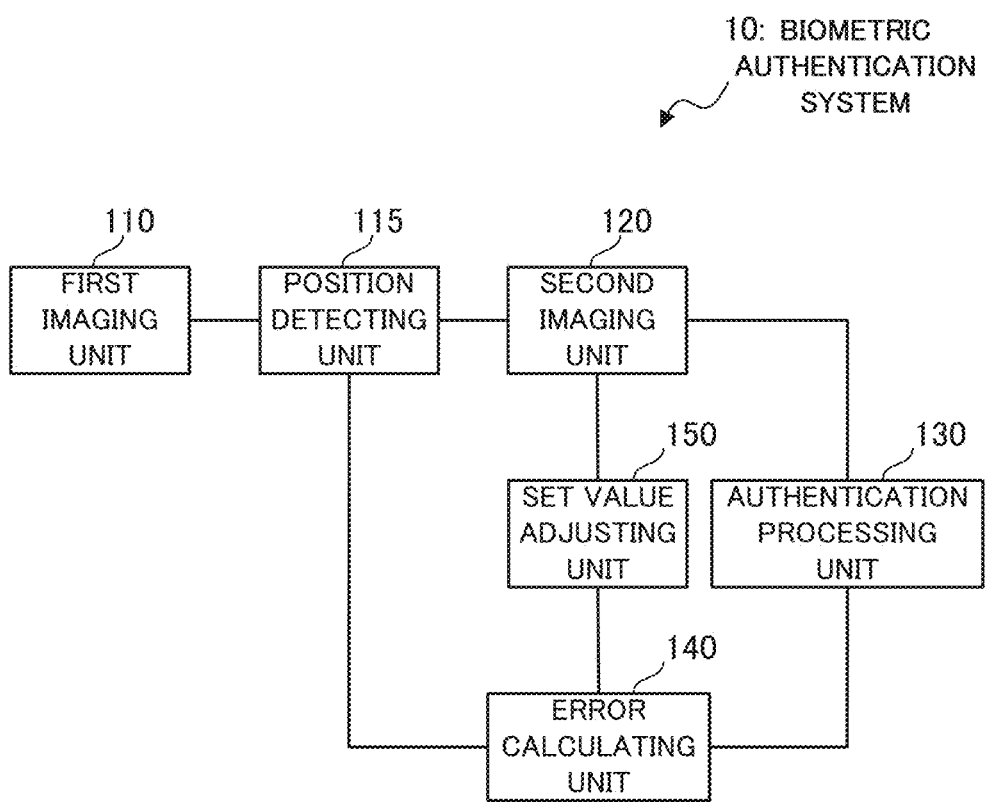
FIG. 2 is a block diagram showing a functional configuration of the biometric authentication system according to the first example embodiment.

Next, referring to FIG. 2, a functional configuration of the biometric authentication system 10 according to the first example embodiment will be described. FIG. 22 is a block diagram showing the functional configuration of the biometric authentication system according to the first example embodiment;

As shown in FIG. 2, the biometric authentication system 10 according to the first example embodiment is configured to comprise as process blocks for realizing the function of the biometric authentication system 10: a first imaging unit 110; a position detecting unit 115; a second imaging unit 120; an authentication processing unit 130; an error calculating unit 140; and a set value adjusting unit 150. The first imaging unit 110 and the second imaging unit 120 each may be configured to include, for example, the camera 20 described above (see FIG. 1). Further, the position detecting unit 115, the authentication processing unit 130, the error calculating unit 140, and the set value adjusting unit 150 each may be realized, for example, in the processor 11 described above (see FIG. 1). The authentication processing unit 130 may not be necessarily provided in the biometric authentication system 10. For example, an apparatus external to the system 10 such as an external server or a cloud system may be configured to comprise the authentication processing unit 130. In this case, the biometric authentication system 10 may be configured to comprise a transmitting unit and a receiving unit to exchange data with the authentication processing unit 130 provided outside the system 10.

The first imaging unit 110 is configured to be capable of imaging a first image including a living body. The first imaging unit 110 is configured to be capable of imaging a wide range as compared with the second imaging unit 120 to be described later. For example, the first imaging unit 110 is configured to be capable of imaging an overall body of the living body that is an imaging target or a relatively wide portion of the living body. The first imaging unit 10 is configured to output the first image taken thereby to the position detecting unit 115.

The position detecting unit 115 is configured to be capable of detecting the position of the living body in the first image. For example, the position detecting unit 115 is configured to be capable of detecting the coordinates of the location where the living body is captured in the first image. However, the position of the living body may be detected as information other than the coordinates. The position of the living body may be detected with reference to a particular portion of the living body. For example, the position of the living body may be detected as the position of the face of the living body. In addition, when two or more living bodies are included in the first image, the position detection unit 115 may detect the position of only one living body as the target, or may detect the positions of all living bodies, respectively. As for the specific method for detecting the position of the living body from an image, since it is possible to appropriately adopt the existing technique, a detailed description thereof will be omitted. The position detecting unit 115 is configured to output the information relating to the position of the living body detected thereby to the second imaging unit 120.

The second imaging unit 120 is configured to be capable of imaging a second image including an authentication portion of the living body. The "authentication portion" here is a portion used in authentication processing implemented by the authentication processing unit 130 to be described later. The second imaging unit 120 is configured to be capable of imaging the second image including the authentication portion, in particular based on the position of the living body in the first image (i.e., the position detected by the position detecting unit 115). The second imaging unit 120 is configured to be capable of changing, for example, an imaging range or gaze region (ROI: Region Of Interest) based on the position of the living body in the first image. The specific configuration for changing the imaging range or gaze region will be described in detail in other example embodiments to be described later. The second imaging unit 12 is configured to output the second image taken thereby to the authentication processing unit 130.

The authentication processing unit 130 is configured to be capable of implementing the authentication processing of the living body by using information relating to the authentication portion contained in the second image. The authentication processing unit 130 compares, for example, information relating to information relating to the authentication portion registered in advance and the information relating to the authentication portion contained in the second image. Then, the authentication processing unit 130. to determine whether or not the living body imaged is the living body registered for the authentication. As for the more specific method of the authentication processing, since it is possible to appropriately adopt the existing technique, a detailed description thereof will be omitted. The authentication processing unit 130 may have a function of outputting an authentication result. In this case, the authentication result may be output by the output apparatus 16 described above (see FIG. 1) or the like. Further, the authentication processing unit 130 according to the present example embodiment, is configured to, in particular, output to the error calculating unit 140, the information relating to the position of the authentication portion used in the authentication.

The error calculating unit 140 is configured to be capable of calculating an error between the first imaging unit 110 and the second imaging unit 120, based on the position of the living body in the first image (i.e., the position detected by the position detecting unit 115) and the position of the authentication portion in the second image. Specifically, the error calculating unit 140 compares the position of the authentication portion estimated from the position of the living body in the first image to the position of the authentication portion in the second image actually imaged, and calculates the displacement amount that the positions are displaced from each other. The error occurring between the first imaging unit 110 and the second imaging unit 120 will be described in detail in other example embodiments to be described later. The error calculating unit 140 is configured to output information relating to the error calculated thereby to the set value adjusting unit 150.

The Set value adjusting unit 150, based on the error between the first imaging unit 110 and the second imaging unit 120 calculated by the error calculating unit 140, is configured to be capable of adjusting a set value relating to the second imaging unit 120. More specifically, the set value adjusting unit 150 adjusts the set value so that the error between the first imaging unit 110 and the second imaging unit 120 is reduced. That is, the set value adjusting unit 150 adjusts the set value so that the displacement between: the position of the authentication portion estimated from the position of the living body in the first image; and the position of the authentication portion in the second image actually taken is reduced. The specific examples of the set value will be described in detail in other example embodiments to be described later.

(Flow of Operation)

Figure 3:
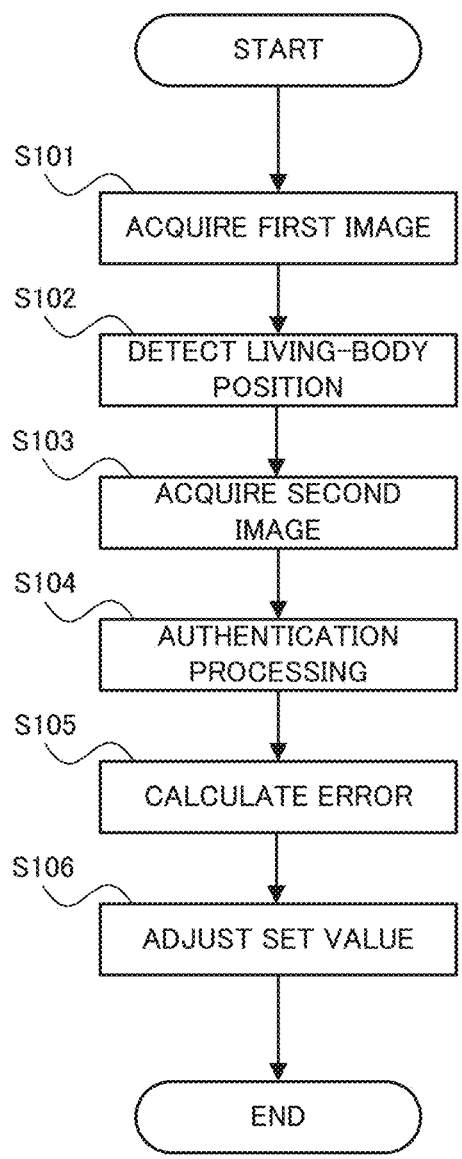
FIG. 3 is a flowchart showing a flow of operation of the biometric authentication system according to the first example embodiment.

Next, referring to FIG. 3, the following description will be given of a flow of operation of biometric authentication system 10 according to the first example embodiment. FIG. 3 is a flow chart showing the flow of the operation of the biometric authentication system according to the first example embodiment;

As shown in FIG. 3, when the biometric authentication system 10 according to the first example embodiment is operated, first, the imaging unit 110 acquires the first image including the living body (step S101). Then, the position detecting unit 115 detects the position of the living body included in the first image acquired (step S102).

Subsequently, the second imaging unit 120 acquires the second image including the authentication portion of the living body based on the detected position of the living body (step S103). Then, the authentication processing unit 130 implements the authentication processing using the information relating to the authentication portion included in the second image (step S104).

Thereafter, the error calculating unit 140 calculates the error between the first imaging unit 110 and the second imaging unit 120 based on the position of the living body in the first image and the position of the authentication portion in the second image (step S105). Then, the set value adjusting unit 150 adjusts the set value relating to the second imaging unit 120, based on the error between the first imaging unit 110 and the second imaging unit 120 calculated (step S106).

(Technical Effects)

Next, technical effects obtained by the biometric authentication system 10 according to the first example embodiment will be described.

As described in FIGS. 1 to 3, in the biometric authentication system 10 according to the first example embodiment, the set value relating to the second imaging unit 120 is adjusted based on the error occurring between the first imaging unit 110 and the second imaging unit 120 (i.e., positional displacement). In this way, even when an error occurs between the first imaging unit 110 and the second imaging unit 120, it is possible to reduce the error.

Second Example Embodiment

The biometric authentication system 10 according to a second example embodiment will be described referring to FIG. 4. The second example embodiment differs in only a part of the operation from the first example embodiment described above. The second example embodiment may have the same configuration as the first example embodiment (see FIGS. 1 and 2). Therefore, in the following, the descriptions for the parts overlapping with the first example embodiment will be omitted as appropriate.

(Flow of Operation)

First, referring to FIG. 4, the following description will be given of a flow of operation of the biometric authentication system 10 according to the second example embodiment. FIG. 4 is a flow chart showing the flow of the operation of the biometric authentication system according to the second example embodiment. In FIG. 4, the reference signs same in FIG. 3 are given to the processes similar to in FIG. 3 respectively.

Figure 4:
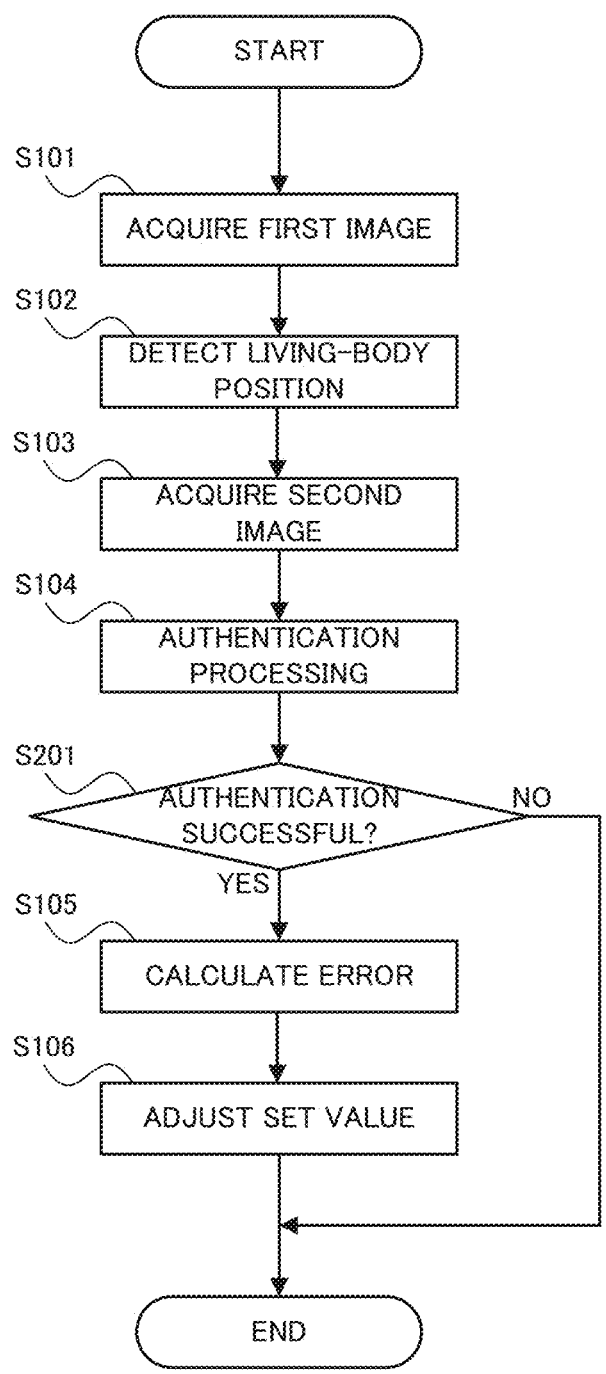
FIG. 4 is a flowchart showing a flow of operation of the biometric authentication system according to the second example embodiment.

As shown in FIG. 4, when the biometric authentication system 10 according to the second example embodiment is operated, first, the imaging unit 110 acquires the first image including the living body (step S101). Then, the position detecting unit 115 detects the position of the living body included in the first image acquired (step S102).

Subsequently, the second imaging unit 120 acquires the second image including the authentication portion of the living body based on the detected position of the living body (step S103). Then, authentication processing unit 130 implements the authentication processing using the authentication portion included in the second image (step S104).

In the second example embodiment, in particular, it is determined whether or not the authentication processing by the authentication processing unit 130 is successful (step S201). When it is determined that the authentication processing is successful (step S201: YES), the error calculating unit 140, calculates an error between the first imaging unit 110 and the second imaging unit 120 based on the position of the living body in the first image and the position of the authentication portion in the second image (step S105). Then, the set value adjusting unit 150 adjusts the set value relating to the second imaging unit 120, based on the error between the first imaging unit 110 and the second imaging unit 120 calculated (step S106).

On the other hand, when it is determined that authentication processing is failed (step S201: NO), the processes of steps S105 and S106 described above are not implemented. That is, neither the error between the first imaging unit 110 and the second imaging unit 120 is calculated, nor the adjustment of the set value based on the calculated error is performed.

(Technical Effects)

Next, technical effects obtained by the biometric authentication system 10 according to the second example embodiment will be described.

As described in FIG. 4, in the biometric authentication system 10 according to the second example embodiment, when the authentication processing is successful, the error between the first imaging unit 110 and the second imaging unit 120 is calculated, and the adjustment of the set value based on the calculated error is performed. When the authentication processing is successful, it is considered that the authentication portion can be recognized at least. Therefore, it can make the error reliably reduced to adjust the set value based on the error. On the other hand, when the authentication processing is failed, there is a possibility that the authentication portion cannot be recognized (i.e., the error may be too large to recognize the authentication portion). Even if an attempt is made to calculate the error in such a case, it is likely that the calculated error is not an appropriate value. Therefore, even if the error is calculated and the set value is adjusted, not only it is not possible to reduce the error, but also there is a possibility that the error rather increases. In the biometric authentication system 10 according to the second example embodiment, since inappropriate situations are eliminated for adjusting the set value as described above, it is possible to reduce the error more reliably.

Third Example Embodiment

The biometric authentication system 10 according to a third example embodiment will be described with reference to FIGS. 5 to 8. The third example embodiment differs only in a part of the configuration and operation from the first and 2 example embodiments described above, and the other parts may be the same as those of the first and 2 example embodiments. Therefore, in the following, the descriptions for parts overlapping with the already described parts will be omitted as appropriate.

(Functional Configuration)

Figure 5:
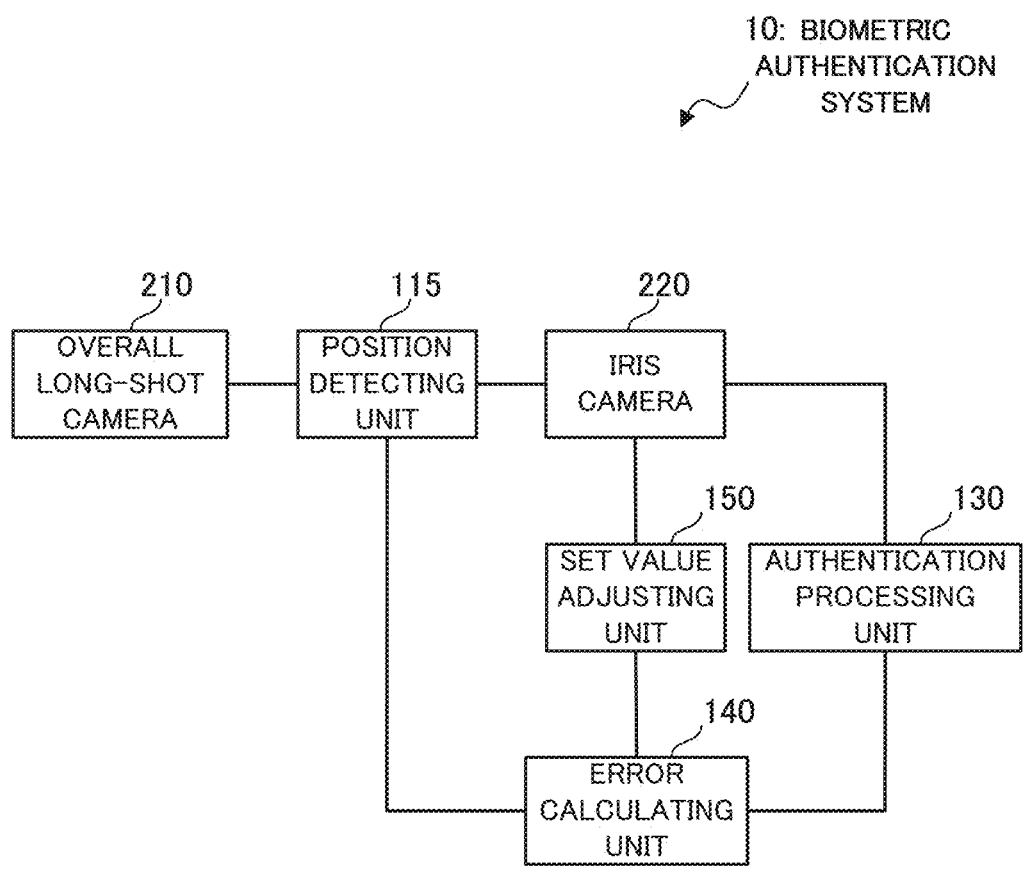
FIG. 5 is a block diagram showing a functional configuration of the biometric authentication system according to the third example embodiment.

First, referring to FIG. 5, the following description will be given of the functional configuration of the biometric authentication system 10 according to the third example embodiment. FIG. 5 is a block diagram showing the functional configuration of the biometric authentication system according to the third example embodiment. In FIG. 5, the reference signs same in FIG. 2 are given to the components similar to in FIG. 2 respectively.

As shown in FIG. 5, the biometric authentication system 10 according to the third example embodiment comprises an overall long-shot camera 210, a position detecting unit 115, an iris camera 220, an authentication processing unit 130, an error calculating unit 140, and a set value adjusting unit 150 as process blocks for realizing the function of the biometric authentication system 10. That is, in the third example embodiment, instead of the first imaging unit 110 according to the first example embodiment, the overall long-shot camera 210 is provided. Further, instead of the second imaging unit 120, the iris camera 220 is provided. The respective the overall long-shot camera 210 and the iris camera 220 may be configured to include, for example, the above-described camera 20 (see FIG. 1).

The overall long-shot camera 210 is configured to be capable of taking an image that includes at least the face of a target person of the authentication processing. The overall long-shot camera 210 is a camera capable of imaging a relatively wide range in a bird's-eye view. The overall long-shot camera 210 may be configured as a camera having an imaging range wider than the iris camera 220. Alternatively, the overall long-shot camera 210 may be positioned or angled so that the imaging range is wider than that of the iris camera. The overall long-shot camera 210 may be set to image the target person, for example, at the timing when the target person passes through a sensor.

The iris camera 220 is configured to be capable of taking an image including the iris of the living body. Therefore, the iris camera 220 is configured as a camera capable of imaging a relatively narrow imaging range with high image quality. The iris camera 220 may be configured as a camera offering more pixels than the overall long-shot camera 210. The iris camera 220 may be configured to cut out an image corresponding to the ROI, which is a part of the imaging range, to acquire the second image. More than one of the iris camera 220 may be installed. In this case, the iris camera 220 to be used for imaging the iris of the living body may be only one selected from the more than one of the iris camera 220.

(Error at the Time of Imaging)

Figure 6:
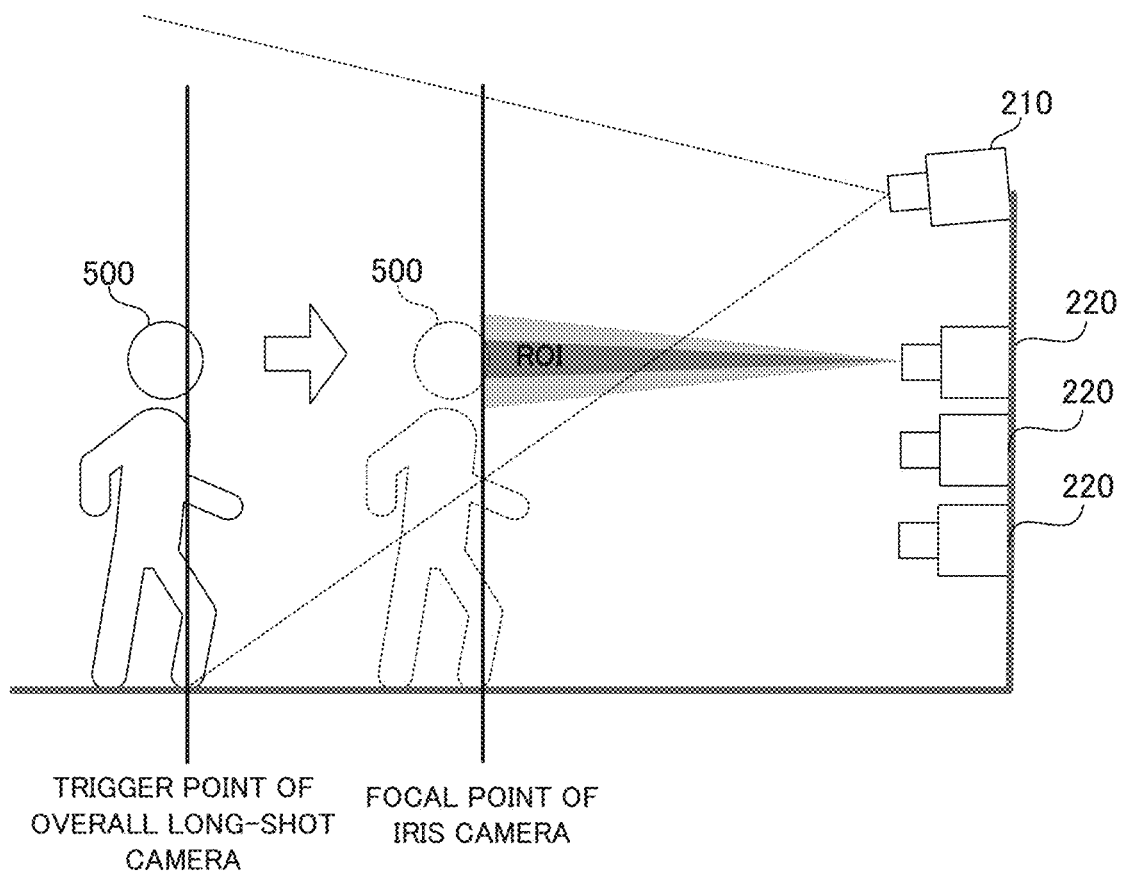
FIG. 6 is a conceptual diagram showing an example of taking images with an overall long-shot camera and an iris camera respectively.
Figure 7:
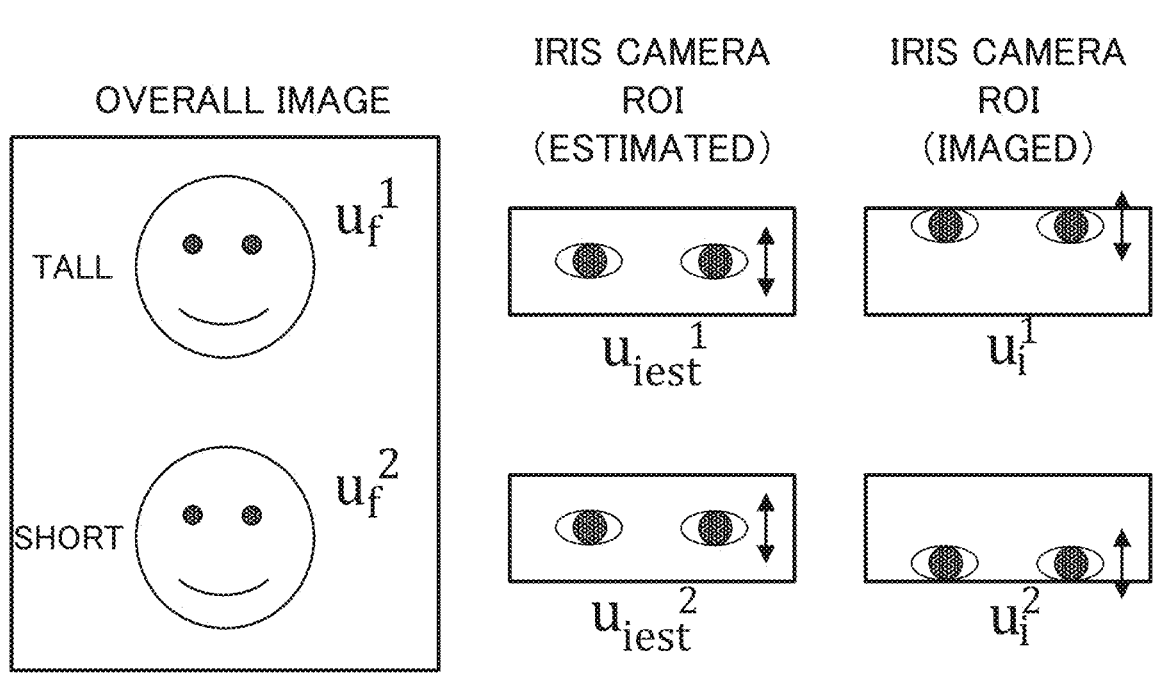
FIG. 7 is a conceptual diagram showing an example of positional displacement occurring with respect to the iris camera.

Next, an example of taking images with the overall long-shot camera 210 and the iris camera 220 respectively, and the error that would occur at that time, will be specifically described with reference to FIGS. 6 and 7. FIG. 6 is a conceptual diagram showing the example of taking images with the overall long-shot camera and the iris camera respectively. FIG. 7 is a conceptual diagram showing an example of the positional displacement occurring in the iris camera.

As shown in FIG. 6, in the biometric authentication system 10 according to the third example embodiment, for example, the target person 500 is imaged using the overall long-shot camera 210 and a plurality of iris cameras 220. It is assumed that the target person 500 moves closer to the overall long-shot camera 210 and the iris cameras 220.

When the target person reaches a trigger point (e.g., a sensor position) of the overall long-shot camera 210, the overall long-shot camera 210 takes the first image. The first image includes the face of the target person 500. The position of the face of the target person 500 in the first image is detected by the position detecting unit 115.

Subsequently, with respect to the iris cameras 220, a single one is selected from the plurality of iris cameras 220 according to the position of the face of the target person 500. Further, the iris camera 220 sets a region of the eyes as the ROI, the region being estimated from the position of the face, and takes the second image at the timing when the target person 500 reaches the focal point of the iris camera 220.

When the first image (an image including the face) and the second image (an iris image) are taken by the above-described configuration, the position of the iris imaged would be sometimes displaced depending on the error between the overall long-shot camera 210 and the iris camera 220.

As shown in FIG. 7, for example, when the target person 500 is tall (i.e., the face is in a relatively high position), the coordinates of eyes in the first image taken by the overall long-shot camera 210 are set as $u_f^1$ and the coordinates of the eyes in the ROI of the iris camera 220 estimated from the coordinates $u_f^1$ are set as $u_{iest}^1$. In this case, compared to the estimated coordinates $u_{iest}^1$ of the eyes, the coordinates $u_i^1$ of the eyes in the ROI actually imaged by the iris camera 220 tends to be displaced upward. On the other hand, when the target person 500 is short (i.e., the face is in a relatively low position), the coordinates of eyes in the first image taken by the overall long-shot camera 210 are set as $u_f^2$ and the coordinates of the eyes in the ROI of the iris camera 220 estimated from the coordinates $u_f^2$ are set as $u_{iest}^2$. In this case, compared to the estimated coordinates $u_{iest}^2$ of the eyes, the coordinates $u_i^2$ of the eyes in the ROI actually imaged by the iris camera 220 tends to be displaced downward.

In the biometric authentication system 10 according to the present example embodiment, the above-described displacement of the coordinates of eyes is calculated as an error, and the set value relating to the iris camera 220 is adjusted. Specifically, correction may be performed according to the displacement of the coordinates so that the error is made small, and the set value may be adjusted according to coordinate information after the correction.

For example, as with the equation (1) shown below, it is sufficient to apply linear corrections to the coordinates $u_f$ of eyes of the overall long-shot camera.

$$u_f = \alpha u'_f + \beta \quad (1)$$

Alternatively, as with the equation (2) shown below, a linear correction may be applied to the estimated coordinates $u_{iest}$ of the iris camera 220.

$$u_{iest} = \gamma u'_{iest} + \delta \quad (2)$$

Each of $\alpha$, $\beta$, $\gamma$, $\delta$ in the above equations (1) and (2) is a correction coefficient, and for example, can be obtained by linear regression or the like from the eye coordinates $u'_f$ and the iris coordinates $u'_{iest}$ which are obtained from the first image.

(Flow of Operation)

Figure 8:
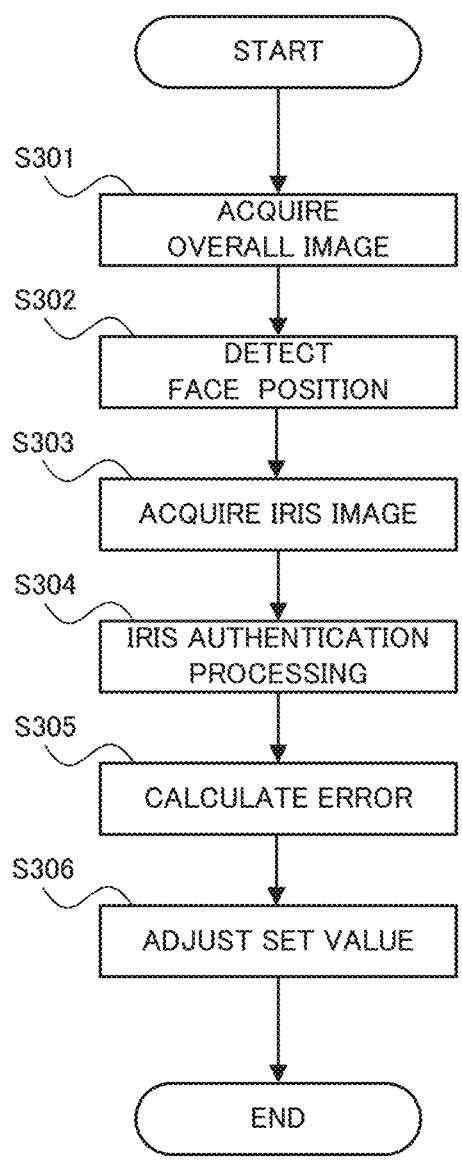
FIG. 8 is a flowchart showing a flow of operation of the biometric authentication system according to the third example embodiment.

Next, referring to FIG. 8, the description will be given of a flow of operation of the biometric authentication system 10 according to the third example embodiment. FIG. 8 is a flow chart showing the flow of the operation of the biometric authentication system according to the third example embodiment. In FIG. 8, the reference signs same in FIG. 3 are given to the processes similar to in FIG. 3 respectively.

As shown in FIG. 8, when the biometric authentication system 10 according to the third example embodiment operates, first, the overall long-shot camera 210 acquires the first image (the overall image) including the face of the living body (step S301). Then, the position detecting unit 115 detects the face position of the living body included in the first image acquired (step S302).

Subsequently, the iris camera 220 acquires the second image (the iris image) including the iris that is the authentication portion, based on the detected face position of the living body (step S303). Then, the authentication processing unit 130 implements the authentication processing using information relating to the iris included in the second image (step S304). That is, the authentication processing unit 130 implements the iris authentication. As for a specific method of the iris authentication, the existing technique can be appropriately adopted, and thus a detailed description thereof will be omitted.

Thereafter, the error calculating unit 140 calculates the error between the overall long-shot camera 210 and the iris camera 220 based on the position of the face of the living body in the first image and the position of the iris in the second image (step S305). Then, the set value adjusting unit 150 adjusts the set value relating to the iris camera 220, based on the error between the overall long-shot camera 210 and the iris camera 220 calculated (step S306).

(Technical Effects)

Next, technical effects obtained by the biometric authentication system 10 according to the third example embodiment will be described.

As described in FIGS. 5 to 8, in the biometric authentication system 10 according to the third example embodiment, the authentication processing (the iris authentication) is performed using the iris image taken by the iris camera 220. The iris authentication requires that the iris of the target person 500 is imaged so as to be contained within a relatively small imaging range. Because of that, when the positional displacement occurs, this situation is likely to prevent normal biometric authentication. However, according to the biometric authentication system 10 of the third example embodiment, since the set value is adjusted based on the positional displacement (the error) of eyes, it is possible to appropriately perform the iris authentication.

Fourth Example Embodiment

The biometric authentication system 10 according to a fourth example embodiment will be described with reference to FIG. 9. In the fourth example embodiment, a specific example of the set value of the iris camera 220 in the third example embodiment will be described. The system configuration and the like of the fourth example embodiment may be the same as those of the first to third example embodiments. Therefore, in the following, the descriptions for parts overlapping with the parts already described will be omitted as appropriate.
(Flow of Operation)

First, referring to FIG. 9, the description will be given of a flow of operation of the biometric authentication system 10 according to the fourth example embodiment. FIG. 9 is a flow chart showing the flow of the operation of the biometric authentication system according to the fourth example embodiment. In FIG. 9, the reference signs same in FIG. 8 are given to the processes similar to in FIG. 8 respectively.

Figure 9:
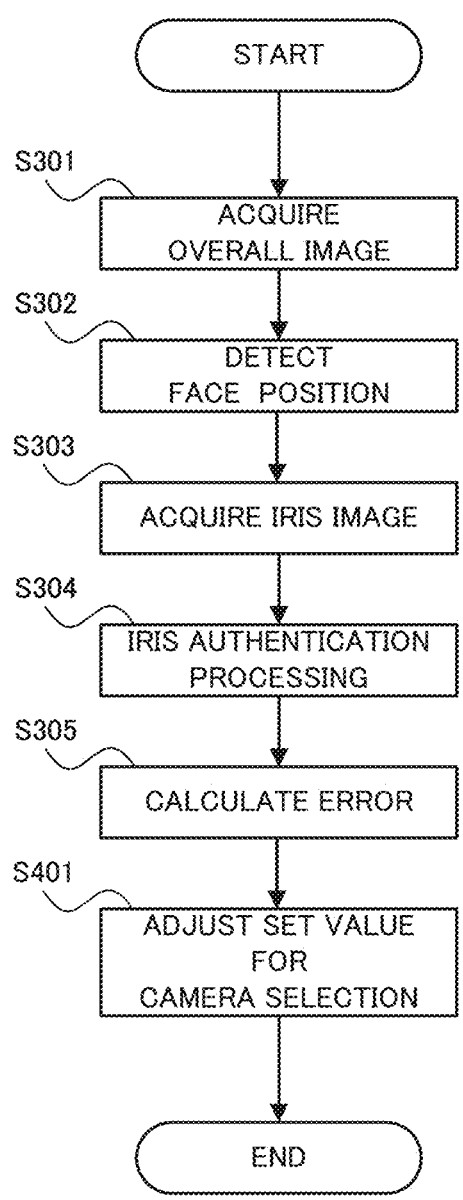
FIG. 9 is a flowchart showing a flow of operation of the biometric authentication system according to the fourth example embodiment.

As shown in FIG. 9, when the biometric authentication system 10 according to the fourth example embodiment operates, first, the overall long-shot camera 210 acquires the first image (the overall image) including the face of the living body (step S301). Then, the position detecting unit 115 detects the face position of the living body included in the first image acquired (step S302). Subsequently, the iris camera 220 acquires the second image (the iris image) including the iris that is the authentication portion, based on the detected face position of the living body (step S303). Then, the authentication processing unit 130 implements the authentication processing using information relating to the iris included in the second image (step S304).

Thereafter, the error calculating unit 140 calculates the error between the overall long-shot camera 210 and the iris camera 220 based on the position of the face of the living body in the first image and the position of the iris in the second image (step S305). Then, the set value adjusting unit 150 adjusts the set value which is used for the selection of the iris camera 220, based on the error between the overall long-shot camera 210 and the iris camera 220 calculated (step S406).

In the biometric authentication system 10 according to the fourth example embodiment, as already described in FIG. 6, the single iris camera is selected from the plurality of iris cameras 220 according to the height of eyes of the target person 500 and the iris image is taken. Accordingly, if the set value to be used for the selection of the iris camera 220 is adjusted, for example, an iris camera 220 other than the iris camera 220 used before the adjustment would be selected.
(Technical Effects)

Next, technical effects obtained by the biometric authentication system 10 according to the fourth example embodiment will be described.

As described in FIG. 9, in the biometric authentication system 10 according to the fourth example embodiment, the set value to be used for the selection of the iris camera 220 is adjusted. In this manner, it is possible to avoid a situation that an inadequate iris camera 220 (e.g., the iris camera 220 that does not actually match the height of eyes of the target person 500) is selected because of the error occurring between the overall long-shot camera 210 and the iris camera 220. Thus, it is possible to perform the biometric authentication (the iris authentication) more appropriately.

Fifth Example Embodiment

The biometric authentication system 10 concerning a fifth example embodiment will be described referring to FIG. 10. In the fifth example embodiment, similarly to the fourth example embodiment, the description will be given of a specific example of the set value of the iris camera 220 in the third example embodiment described above. The system configuration and the like may be the same as those of the first to third example embodiments. Therefore, in the following, the descriptions for parts overlapping with the parts already described will be omitted as appropriate.
(Flow of Operation)

First, referring to FIG. 10, the description will be given of a flow of operation of the biometric authentication system 10 according to the fifth example embodiment. FIG. 10 is a flow chart showing the flow of the operation of the biometric authentication system according to the fifth example embodiment. In FIG. 10, the reference signs same in FIG. 8 are given to the processes similar to in FIG. 8 respectively.

Figure 10:
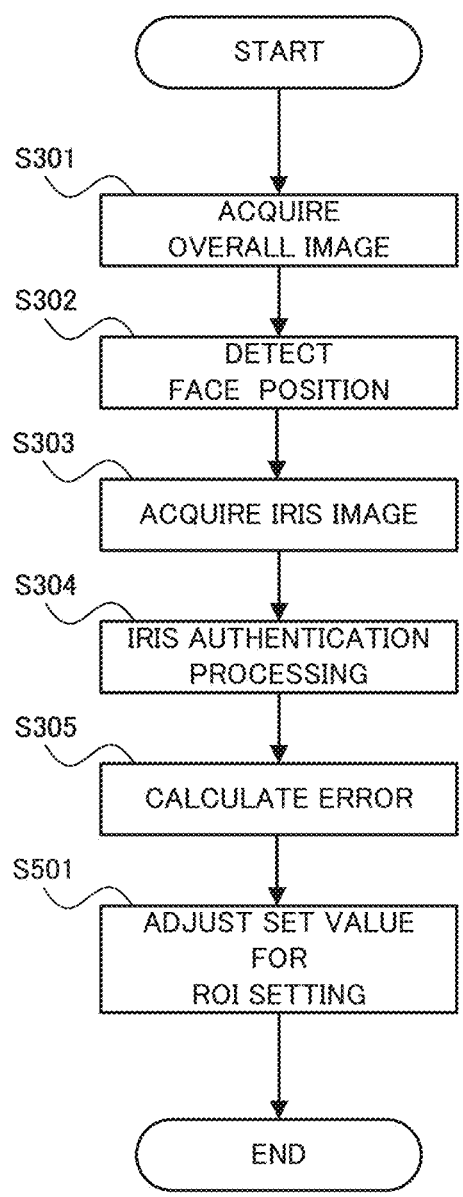
FIG. 10 is a flowchart showing a flow of operation of the biometric authentication system according to the fifth example embodiment.

As shown in FIG. 10, when the biometric authentication system 10 according to the fifth example embodiment operates, first, the overall long-shot camera 210 acquires the first image (the overall image) including the face of the living body (step S301). Then, the position detecting unit 115 detects the face position of the living body included in the first image acquired (step S302).

Subsequently, the iris camera 220 acquires the second image (the iris image) including the iris that is the authentication portion, based on the detected face position of the living body (step S303). Then, the authentication processing unit 130 implements the authentication processing using information relating to the iris included in the second image (step S304).

Thereafter, the error calculating unit 140 calculates the error between the overall long-shot camera 210 and the iris camera 220 based on the position of the face of the living body in the first image and the position of the iris in the second image (step S305). Then, the set value adjusting unit 150 adjusts the set value which is used for the setting of the ROI, based on the error between the overall long-shot camera 210 and the iris camera 220 calculated (step S506).

In the biometric authentication system 10 according to the fifth example embodiment, as already described in FIG. 6, the ROI (the region corresponding to the height of eyes of the target person 500) of the iris camera 220 is set and the iris image is taken. Therefore, by adjusting the set value for the setting of the ROI, for example, an ROI other than the ROI used before the adjustment would be set.

Although an example in which the ROI is automatically set has been described here, the setting of the ROI after adjusting the set value may be performed manually. For example, information relating to the ROI according to the adjusted set value (for example, information on the size and position of the ROI) may be displayed on a user terminal (for example, a display apparatus of a personal computer or a portable terminal of the system administrator). In this case, the user who has confirmed the information relating to the ROI on the user terminal may manually set the ROI of the iris camera 220 based on the information displayed.

(Technical Effects)

Next, technical effects obtained by the biometric authentication system 10 according to the fifth example embodiment will be described.

As described in FIG. 10, in the biometric authentication system 10 according to the fifth example embodiment, the set value to be used for the selecting of the ROI is adjusted. In this manner, it is possible to avoid a situation that an inadequate ROI (e.g., the ROI that does not actually match the height of eyes of the target person 500) is set because of the error between the overall long-shot camera 210 and the iris camera 220. Thus, it is possible to perform the biometric authentication (the iris authentication) more appropriately.

Sixth Example Embodiment

The biometric authentication system 10 according to a sixth example embodiment will be described referring to FIG. 11. In the sixth example embodiment, similarly to the fourth and the fifth example embodiments, the description will be given of a specific example of the set value of the iris camera 220 in the third example embodiment described above. The system configuration and the like may be the same as those of the first to third example embodiments. Therefore, in the following, the descriptions for parts overlapping with the parts already described will be omitted as appropriate.

(Flow of Operation)

First, referring to FIG. 11, the description will be given of a flow of operation of the biometric authentication system 10 according to the sixth example embodiment. FIG. 11 is a flow chart showing the flow of the operation of the biometric authentication system according to the sixth example embodiment. In FIG. 11, the reference signs same in FIG. 8 are given to the processes similar to in FIG. 8 respectively.

Figure 11:
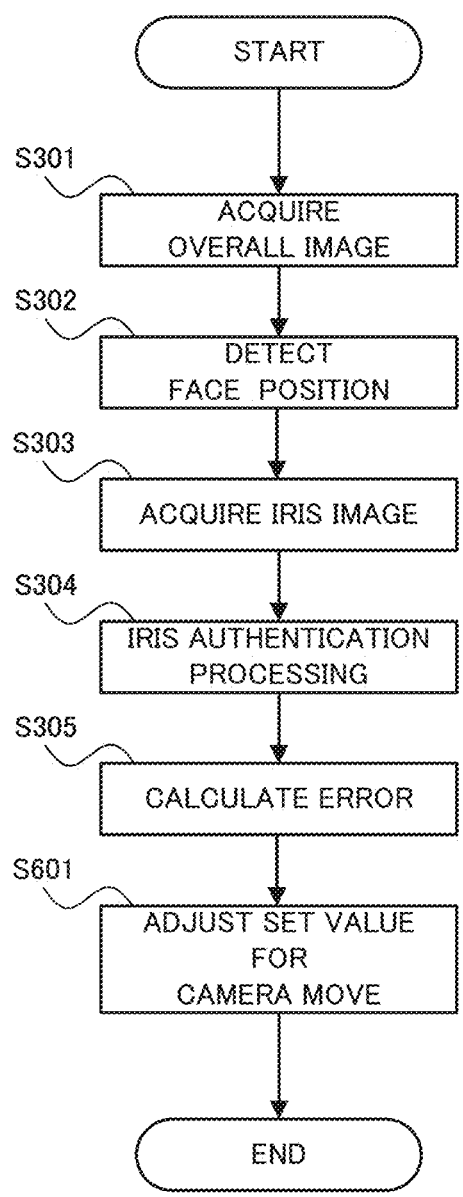
FIG. 11 is a flowchart showing a flow of operation of the biometric authentication system according to the sixth example embodiment.

As shown in FIG. 11, when the biometric authentication system 10 according to the sixth example embodiment operates, first, the overall long-shot camera 210 acquires the first image (the overall image) including the face of the living body (step S301). Then, the position detecting unit 115 detects the face position of the living body included in the first image acquired (step S302).

Subsequently, the iris camera 220 acquires the second image (the iris image) including the iris that is the authentication portion, based on the detected face position of the living body (step S303). Then, the authentication processing unit 130 implements the authentication processing using information relating to the iris included in the second image (step S304).

Thereafter, the error calculating unit 140 calculates the error between the overall long-shot camera 210 and the iris camera 220 based on the position of the face of the living body in the first image and the position of the iris in the second image (step S305). Then, the set value adjusting unit 150 adjusts the set value which is used for the move of the iris camera 220, based on the error between the overall long-shot camera 210 and the iris camera 220 calculated (step S606).

In the biometric authentication system 10 according to the sixth example embodiment, by moving the iris camera 220 (e.g., by sliding movement or changing the tilt angle), it is allowed for at least one of the position and the angle of the iris camera 220 to change. Therefore, if the set value to be used for the move of the iris camera 220 is adjusted, for example, the iris image would be imaged in an imaging range other than the imaging range used before the adjustment.

Although an example in which the camera is moved automatically has been described here, the movement of the camera after adjusting the set value may be performed manually. For example, the position information of the camera according to the set value after the adjustment (e.g., such as rotating by 0 degrees in the pan direction or the tilt direction) may be displayed on a user terminal (e.g., a display apparatus of a personal computer or portable terminal of the system manager). In this case, the user who has confirmed the position information of the camera on the user terminal may manually move the iris camera 220 based on the information displayed.

(Technical Effects)

Next, technical effects obtained by the biometric authentication system 10 according to the sixth example embodiment will be described.

As described in FIG. 11, in the biometric authentication system 10 according to the sixth example embodiment, the set value to be used for the move of the iris camera 220 is adjusted. In this manner, it is possible to avoid a situation that the iris image is taken in an inadequate imaging range (e.g., an imaging range that does not actually match the height of eyes of the target person 500) because of the error between the overall long-shot camera 210 and the iris camera 220. Thus, it is possible to perform the biometric authentication (the iris authentication) more appropriately.

Seventh Example Embodiment

The biometric authentication system 10 according to a seventh example embodiment will be described with reference to FIGS. 12 to 14. The seventh example embodiment differs only in a part of the configuration and operation from the first to the sixth example embodiments described above, and the other parts may be the same as those of the first to the sixth example embodiments. Therefore, in the following, the descriptions for parts overlapping with the already described parts will be omitted as appropriate.

(Functional Configuration)

First, referring to FIG. 12, the following description will be given of the functional configuration of the biometric authentication system 10 according to the seventh example embodiment. FIG. 12 is a block diagram showing the functional configuration of the biometric authentication system according to the seventh example embodiment. In FIG. 12, the reference signs same in FIG. 5 are given to the components similar to in FIG. 5 respectively.

Figure 12:
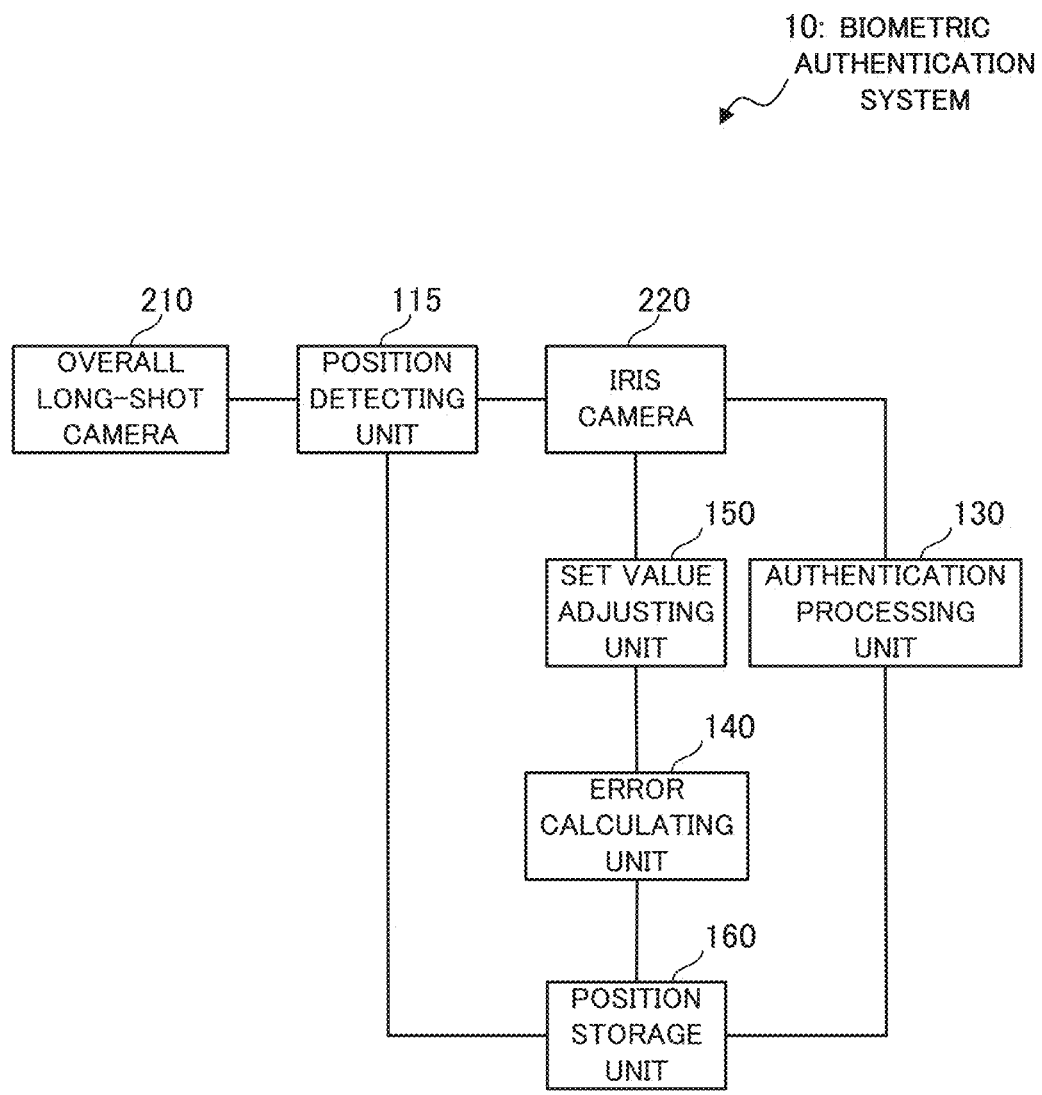
FIG. 12 is a block diagram showing a functional configuration of the biometric authentication system according to the seventh example embodiment.

As shown in FIG. 12, the biometric authentication system 10 according to the seventh example embodiment comprises an overall long-shot camera 210, a position detecting unit 115, an iris camera 220, an authentication processing unit 130, an error calculating unit 140, a set value adjusting unit 150, and a position storage unit 160 as process blocks for realizing the function of the biometric authentication system 10. That is, the seventh example embodiment is configured to further add the position storage unit 160 to the components in the third example embodiment (see FIG. 5). The position storage unit 160 may be configured to include, for example, the above-described storage apparatus 14 (see FIG. 1).

The position storage unit 160 is configured to be capable of storing the position of the face of the living body in the first image and the position of the iris in the second image in association with each other. Alternatively, the position storage unit 160 may be configured to be capable of storing the position of the iris estimated from the position of the face of the living body in the first image and the position of the iris in the second image in association with each other. The position storage unit 160 is typically configured to be capable of storing a plurality of sets of combination of the above-described position information. The position storage unit 160 may have a function of deleting unnecessary information (e.g., the oldest information within stored information, etc.). The position information stored in the position storage unit 160 is allowed to be read out as appropriate by the error calculating unit 140.

(Flow of Operation)

Next, referring to FIG. 13, the description will be given of a flow of operation of the biometric authentication system 10 according to the seventh example embodiment. FIG. 13 is a flow chart showing the flow of the operation of the biometric authentication system according to the seventh example embodiment. In FIG. 13, the reference signs same in FIG. 8 are given to the processes similar to in FIG. 8 respectively.

Figure 13:
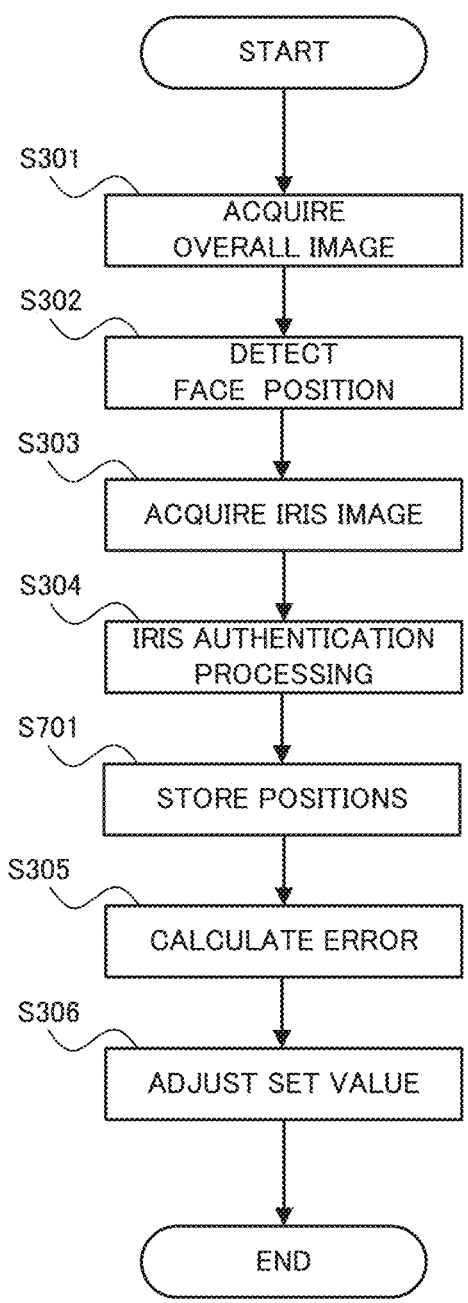
FIG. 13 is a flowchart showing a flow of operation of the biometric authentication system according to the seventh example embodiment.

As shown in FIG. 13, when the biometric authentication system 10 according to the seventh example embodiment operates, first, the overall long-shot camera 210 acquires the first image (the overall image) including the face of the living body (step S301). Then, the position detecting unit 115 detects the face position of the living body included in the first image acquired (step S302).

Subsequently, the iris camera 220 acquires the second image (the iris image) including the iris that is the authentication portion, based on the detected face position of the living body (step S303). Then, the authentication processing unit 130 implements the authentication processing using information relating to the iris included in the second image (step S304).

In the seventh example embodiment, in particular, the position storage unit 160 stores the position of the face of the living body in the first image and the position of the iris in the second image in association with each other (step S701).

Thereafter, the error calculating unit 140 reads out the position of the face of the living body in the first image and the position of the iris in the second image which are stored in the position storage unit 160, and then calculates the error between the overall long-shot camera 210 and the iris camera 220 (step S305). Then, the set value adjusting unit 150 adjusts the set value relating to the iris camera 220, based on the error between the overall long-shot camera 210 and the iris camera 220 calculated (step S306).

(Modification)

Next, referring to FIG. 14, the description will be given of a flow of operation of the biometric authentication system 10 according to a modification of the seventh example embodiment. FIG. 14 is a flow chart showing the flow of the operation of the biometric authentication system according to the modification of the seventh example embodiment. In FIG. 14, the reference signs same in FIG. 13 are given to the processes similar to in FIG. 13 respectively.

Figure 14:
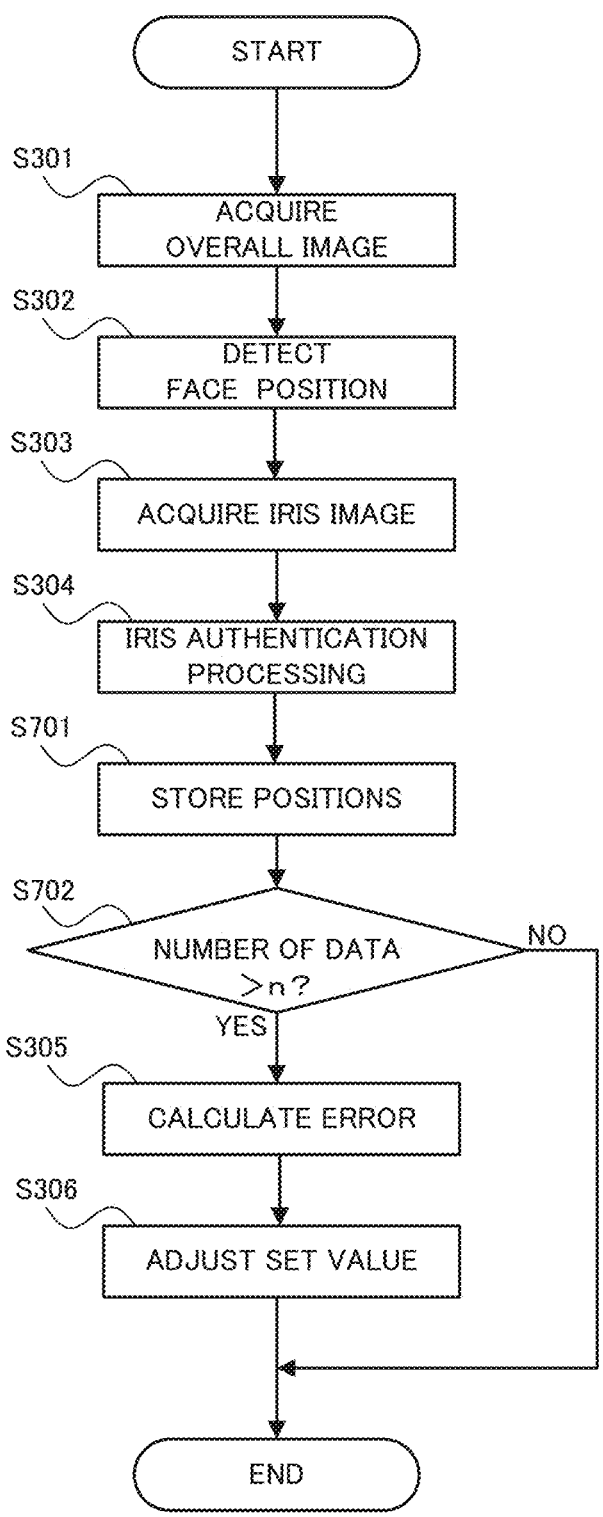
FIG. 14 is a flowchart showing a flow of operation of the biometric authentication system according to a modification of the seventh example embodiment.

As shown in FIG. 14, when the biometric authentication system 10 according to the modification of the seventh example embodiment operates, first, the overall long-shot camera 210 acquires the first image (the overall image) including the face of the living body (step S301). Then, the position detecting unit 115 detects the face position of the living body included in the first image acquired (step S302).

Subsequently, the iris camera 220 acquires the second image (the iris image) including the iris that is the authentication portion, based on the detected face position of the living body (step S303). Then, the authentication processing unit 130 implements the authentication processing using information relating to the iris included in the second image (step S304).

Subsequently, the position storage unit 160 stores the position of the face of the living body in the first image and the position of the iris in the second image in association with each other (step S701). Then, the position storage unit 160 determines whether the number of stored data (i.e., the number of pairs of the position information) is larger than a predetermined number n (step S702). Here, the predetermined number n is a threshold value for determining whether data sufficient to calculate the error has been accumulated. The predetermined number n may be prepared in advance by a prior simulation or the like.

When it is determined that the number of stored data is larger than n (step S702: YES), the error calculating unit 140 reads out the position of the face of the living body in the first image and the position of the iris in the second image which are stored in the position storage unit 160, and then calculates the error between the overall long-shot camera 210 and the iris camera 220 (step S305). Then, the set value adjusting unit 150 adjusts the set value relating to the iris camera 220, based on the error between the overall long-shot camera 210 and the iris camera 220 calculated (step S306).

On the other hand, when it is not determined that the number of stored data is greater than n (step S702: NO), the processes of steps S305 and S306 described above are not implemented. That is, neither the error between the overall long-shot camera 210 and the iris camera 220 is calculated, nor the adjustment of the set value based on the calculated error is performed.

(Technical Effects)

Next, technical effects obtained by the biometric authentication system 10 according to the seventh example embodiment will be described.

As described in FIGS. 12 to 14, in the biometric authentication system 10 according to the seventh example embodiment, the position of the face of the living body in the first image and the position of the iris in the second image are stored. In this way, it is possible to calculate the error and adjust the set value at a timing different from the timing of performing the authentication processing. Therefore, for example, it is possible to a little while after implementing the authentication processing, it is possible to calculate the error and adjust the set value. Further, as described in the modification, if the processing is set so as to be implemented after accumulating the predetermined number of data, it is possible to calculate the error and adjust the set value at a more appropriate timing. In addition, it is possible to reduce the processing load of the system compared to a case that the error is calculated each time the authentication processing is implemented.

Eighth Example Embodiment

The biometric authentication system 10 according to an eighth example embodiment will be described with reference to FIG. 15 and FIG. 16. The eighth example embodiment differs only in a part of the configuration and operation from the first to the seventh example embodiments described above, and the other parts may be the same as those of the first to the seventh example embodiments. Therefore, in the following, the descriptions for parts overlapping with the already described parts will be omitted as appropriate.

(Functional Configuration)

First, referring to FIG. 15, the following description will be given of the functional configuration of the biometric authentication system 10 according to the eighth example embodiment. FIG. 15 is a block diagram showing the functional configuration of the biometric authentication system according to the eighth example embodiment. In FIG. 15, the reference signs same in FIG. 2 are given to the components similar to in FIG. 2 respectively.

Figure 15:
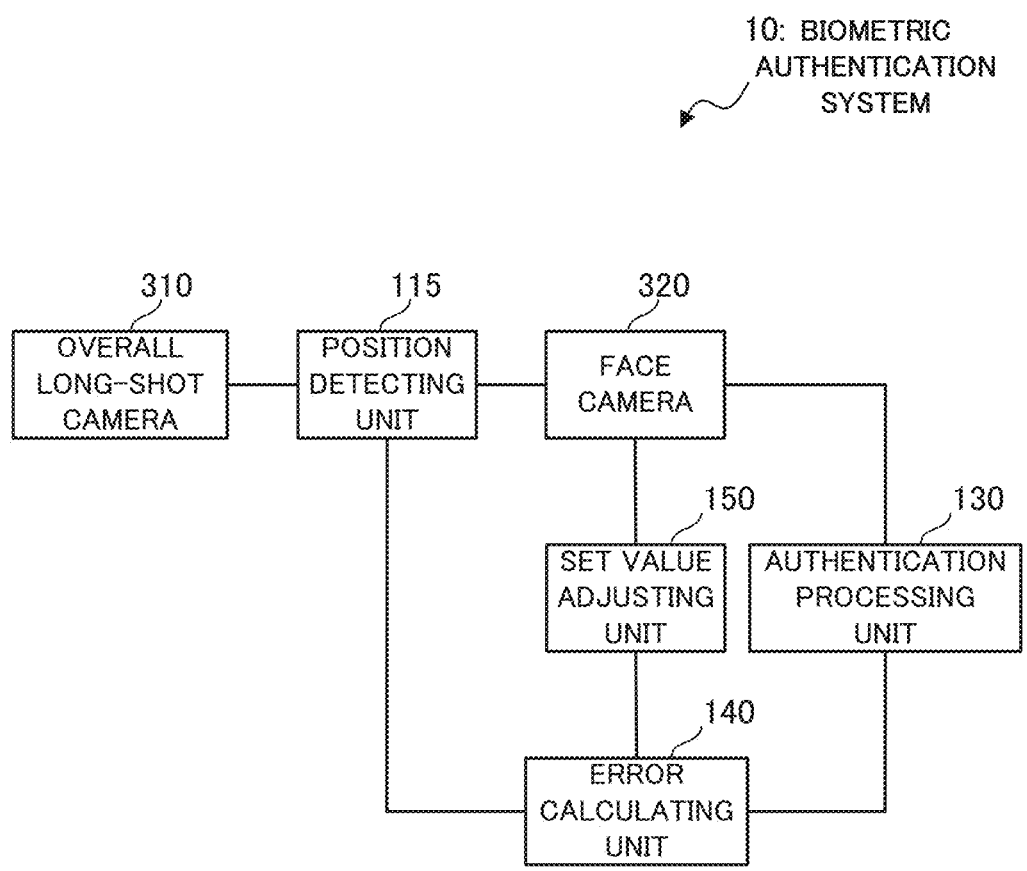
FIG. 15 is a block diagram showing a functional configuration of the biometric authentication system according to the eighth example embodiment.

As shown in FIG. 15, the biometric authentication system 10 according to the eighth example embodiment comprises an overall long-shot camera 310, a position detecting unit 115, a face camera 320, an authentication processing unit 130, an error calculating unit 140, and a set value adjusting unit 150 as process blocks for realizing the function of the biometric authentication system 10. That is, in the eighth example embodiment, instead of the first imaging unit 110 according to the first example embodiment, the overall long-shot camera 310 is provided. Further, instead of the second imaging unit 120, the face camera 320 is provided. The respective the overall long-shot camera 310 and the face camera 320 may be configured to include, for example, the above-described camera 20 (see FIG. 1).

The overall long-shot camera 310 is configured to be capable of taking an image including at least the face of the target person, similarly to the overall long-shot camera 210 in the third example embodiment. However, the overall long-shot camera 310 according to the eighth example embodiment is configured to be capable of containing more than one of the living body in the imaging range. For example, the overall long-shot camera 310 is configured to be capable of imaging faces of people existing in a relatively large room, venue or the like. The overall long-shot camera 310 is configured to output to the position detecting unit 115, the first image including a plurality of living bodies imaged by the overhead long-shot camera 310. The position detecting unit 115 detects from the first image, the position of the target person 500 included in the plurality of living bodies.

The face camera 320 is configured to be capable of taking an image including the face of the target person 500. The face camera 320 may be configured as a camera capable of imaging a narrower imaging range than the overall long-shot camera 310. The face camera 320 is particularly configured to be capable of imaging the second image including the face of the target person 500, based on the position of the target person 500 in the first image (i.e., the position detected from the first image by the position detecting unit 115). The face camera 320 is configured to be capable of changing, for example, the imaging range or the gaze region, based on the position of the target person 500 in the first image. More than one of the face camera 320 may be installed. In this case, the face camera 320 to be used for imaging the face of the living body may be only one selected from the more than one of the face camera 320.

(Flow of Operation)

Next, referring to FIG. 16, the description will be given of a flow of operation of the biometric authentication system 10 according to the eighth example embodiment. FIG. 16 is a flow chart showing the flow of the operation of the biometric authentication system according to the eighth example embodiment. In FIG. 16, the reference signs same in FIG. 3 are given to the processes similar to in FIG. 3 respectively.

Figure 16:
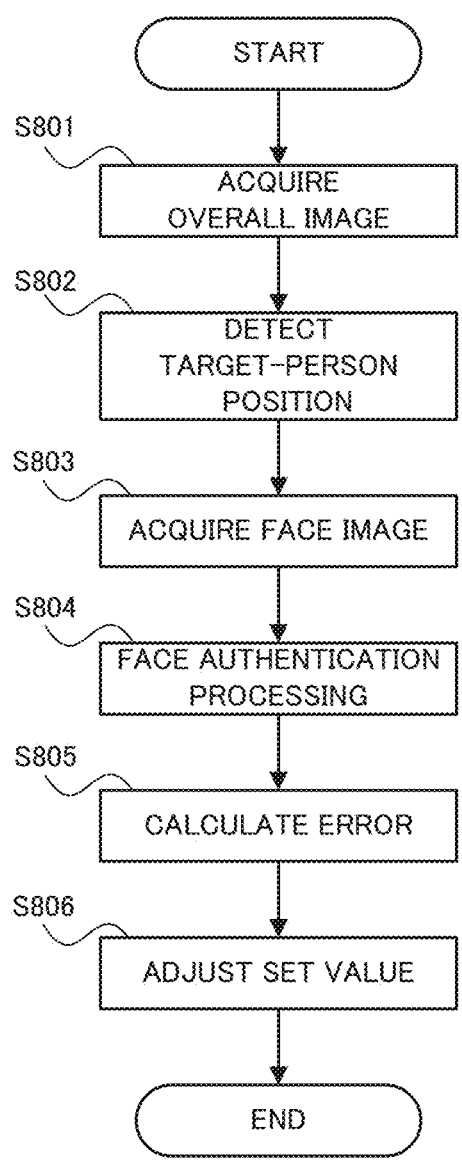
FIG. 16 is a flowchart showing a flow of operation of the biometric authentication system according to the eighth example embodiment.

As shown in FIG. 16, when the biometric authentication system 10 according to the eighth example embodiment operates, first, the overall long-shot camera 310 acquires the first image (the overall image) including the plurality of living bodies (step S801). Then, the position detecting unit 115 detects the position of a single target person 500 who is the target of the authentication processing from the plurality of living bodies included in the first image acquired (step S802).

Subsequently, the face camera 320 acquires the second image (a face image) including the face of the target person that is the authentication portion, based on the detected position of the living body (step S803). Then, the authentication processing unit 130 implements the authentication processing using information relating to the face of the target person 500 included in the second image (step S804). That is, the authentication processing unit 130 implements the face authentication. As for a specific method of the face authentication, the existing technique can be appropriately adopted, and thus a detailed description thereof will be omitted.

Thereafter, the error calculating unit 140 calculates the error between the overall long-shot camera 310 and the face camera 320 based on the position of the target person 500 in the first image and the position of the face of the target person 500 in the second image (step S805). More specifically, the error calculating unit 140 calculates the amount of displacement between: the position of the face of the target person estimated from the position of the target person 500 in the first image; and the position the position of the face of the target person 500 actually taken in the second image. Then, the set value adjusting unit 150 adjusts the set value relating to the face camera 320, based on the error between the overall long-shot camera 310 and the face camera 320 calculated (step S306).

(Technical Effects)

Next, technical effects obtained by the biometric authentication system 10 according to the eighth example embodiment will be described.

As described in FIGS. 15 and 16, in the biometric authentication system 10 according to the eighth example embodiment, the authentication processing (the face authentication) is implemented using the face image taken by the face camera 320. The face authentication according to the eighth example embodiment requires that a single target person 500 is specified from a plurality of living bodies, and the face of the single target person 500 is imaged. Because of that when the positional displacement occurs, it is likely that normal biometric authentication cannot be performed. However, according to the biometric authentication system 10 according to the eighth example embodiment, since the set value is adjusted based on the positional displacement (the error) of the position of the face of the target person, it is possible to appropriately perform the face authentication.

<Supplementary Note>

With respect to the example embodiments described above, they may be further described as the following supplementary notes, but are not limited to the following.

(Supplementary Note 1)

A biometric authentication system disclosed in the supplementary note 1 is a biometric authentication system comprising: a first imaging unit that images a first image including a living body; a detecting unit that detects a position of the living body in the first image; a second imaging unit that images a second image including an authentication portion of the living body, based on the position of the living body in the first image; a calculating unit that calculates an error between the first imaging unit and the second imaging unit based on the position of the living body in the first image and a position of the authentication portion in the second image; and an adjusting unit that adjusts a set value relating to the second imaging unit, based on the error.

(Supplementary Note 2)

The biometric authentication system disclosed in the supplementary note 2 is the biometric authentication system according to the supplementary note 1, further comprising an authentication unit that performs authentication processing relating to the living body, using information relating to the authentication portion in the second image.

(Supplementary Note 3)

The biometric authentication system disclosed in the supplementary note 3 is the biometric authentication system according to the supplementary note 2, wherein the calculating unit calculates the error when the authentication processing by the authentication unit is successful.

(Supplementary Note 4)

The biometric authentication system disclosed in the supplementary note 4 is the biometric authentication system according to any one of the supplementary notes 1 to 3, wherein the second imaging unit includes a plurality of cameras, and the set value is a parameter that indicates which camera of the plurality of cameras should be used for taking the second image.

(Supplementary Note 5)

The biometric authentication system disclosed in the supplementary note 5 is the biometric authentication system according to any one of the supplementary notes 1 to 4, wherein the second imaging unit is capable of taking the second image by cutting out a particular region of an imaging range, and the set value is a parameter that indicates which portion of the imaging range should be set to the particular region.

(Supplementary Note 6)

The biometric authentication system disclosed in the supplementary note 6 is the biometric authentication system according to any one of the supplementary notes 1 to 5, wherein the second imaging unit is capable of changing at least one of a position and an angle thereof, and the set value is a parameter that determines the at least one of the position and the angle with respect to the second imaging unit.

(Supplementary Note 7)

The biometric authentication system disclosed in the supplementary note 7 is the biometric authentication system according to any one of the supplementary notes 1 to 6, further comprising a storage unit that is capable of storing the position of the living body in the first image and the position of the authentication portion in the second image, wherein the calculating unit calculates the error based on the position of the living body and the position of the authentication portion stored in the storage unit.

(Supplementary Note 8)

The biometric authentication system disclosed in the supplementary note 8 is the biometric authentication system according to any one of the supplementary notes 1 to 7, wherein the second imaging unit images the second image including an iris of the living body that is the authentication portion, based on a position of a face of the living body in the first image.

(Supplementary Note 9)

The biometric authentication system disclosed in the supplementary note 9 is the biometric authentication system according to any one of the supplementary notes 1 to 7, wherein the second imaging unit images the second image including a face of the living body that is the authentication portion, based on the position of the living body in the first image.

(Supplementary Note 10)

A biometric authentication method disclosed in the supplementary note 10 is a biometric authentication method comprising: imaging a first image including a living body with a first imaging unit; detecting a position of the living body in the first image; imaging with a second imaging unit, a second image including an authentication portion of the living body, based on the position of the living body in the first image; calculating an error between the first imaging unit and the second imaging unit based on the position of the living body in the first image and a position of the authentication portion in the second image; and adjusting a set value relating to the second imaging unit, based on the error.

(Supplementary Note 11)

A computer program disclosed in the supplementary note 11 is a computer program that causes a computer to perform the following operations: imaging a first image including a living body with a first imaging unit; detecting a position of the living body in the first image; imaging with a second imaging unit, a second image including an authentication portion of the living body, based on the position of the living body in the first image; calculating an error between the first imaging unit and the second imaging unit based on the position of the living body in the first image and a position of the authentication portion in the second image; and adjusting a set value relating to the second imaging unit, based on the error.

(Supplementary Note 12)

A recording medium disclosed in the supplementary note 12 is a recording medium storing the computer program disclosed in the supplementary note 11.

This disclosure is not limited to the above example embodiments. This disclosure can be modified as necessary to the extent that does not contradict the concept or idea of the invention which can be read from the entire claims and the entire description; and biometric authentication systems, biometric authentication methods, computer programs, and recording media with such changes are also included in the technical concept of this disclosure.

To the extent permitted by law, the present application claims priority based on JP 2021-024286, filed on Feb. 18, 2021, and incorporates all of its disclosure herein. Also, to the extent permitted by legislation, all publications and articles described in the present description are incorporated herein by reference.

DESCRIPTION OF REFERENCE SIGNS

10 Biometric Authentication System
110 First Imaging Unit
120 Second Imaging Unit
130 Authentication Processing Unit
140 Error Calculating Unit
150 Set Value Adjusting Unit
160 Position Storage Unit
210 Overall Long-shot Camera
220 Iris Camera
310 Overall Long-shot Camera
320 Face Camera
500 Target Person

What is claimed is:

1. A biometric authentication system comprising:
at least one memory configured to store instructions; and
at least one processor configured to implement the instructions to:
image a first image including a living body with a first imaging unit;
detect a position of the living body in the first image;
image with a second imaging unit, a second image including an authentication portion of the living body, based on the position of the living body in the first image;
calculate an error between the first imaging unit and the second imaging unit based on the position of the living body in the first image and a position of the authentication portion in the second image; and adjust a set value relating to the second imaging unit, based on the error.

2. The biometric authentication system according to claim 1, wherein the at least one processor is further configured to implement the instructions to:
perform authentication processing relating to the living body, using information relating to the authentication portion in the second image.

3. The biometric authentication system according to claim 2, wherein
the at least one processor is configured to implement the instructions to
calculate the error when the authentication processing is successful.

4. The biometric authentication system according to claim 1, wherein
the second imaging unit includes a plurality of cameras, and
the set value is a parameter that indicates which camera of the plurality of cameras should be used for taking the second image.

5. The biometric authentication system according to claim 1, wherein the at least one processor is configured to implement the instructions to
take the second image by cutting out a particular region of an imaging range with the second imaging unit, and
the set value is a parameter that indicates which portion of the imaging range should be set to the particular region.

6. The biometric authentication system according to claim 1, wherein
the at least one processor is configured to implement the instructions to
change at least one of a position and an angle of the second imaging unit, and
the set value is a parameter that determines the at least one of the position and the angle with respect to the second imaging unit.

7. The biometric authentication system according to claim 1, further comprising
a storage unit that is capable of storing the position of the living body in the first image and the position of the authentication portion in the second image, wherein
the at least one processor is configured to implement the instructions to calculate the error based on the position of the living body and the position of the authentication portion stored in the storage unit.

8. The biometric authentication system according to claim 1, wherein
the at least one processor is configured to implement the instructions to
image with the second imaging unit, the second image including an iris of the living body that is the authentication portion, based on a position of a face of the living body in the first image.

9. The biometric authentication system according to claim 1, wherein
the at least one processor is configured to implement the instructions to
with the second imaging unit, the second image including a face of the living body that is the authentication portion, based on the position of the living body in the first image.

10. A biometric authentication method comprising:
imaging a first image including a living body with a first imaging unit;
detecting a position of the living body in the first image;
imaging with a second imaging unit, a second image including an authentication portion of the living body, based on the position of the living body in the first image;
calculating an error between the first imaging unit and the second imaging unit based on the position of the living body in the first image and a position of the authentication portion in the second image; and
adjusting a set value relating to the second imaging unit, based on the error.

11. A non-transitory recording medium storing a computer program that causes a computer to perform the following operations:
imaging a first image including a living body with a first imaging unit;
detecting a position of the living body in the first image;
imaging with a second imaging unit, a second image including an authentication portion of the living body, based on the position of the living body in the first image;
calculating an error between the first imaging unit and the second imaging unit based on the position of the living body in the first image and a position of the authentication portion in the second image; and
adjusting a set value relating to the second imaging unit, based on the error.

* * * * *